United States Patent
Liran et al.

(12)

(10) Patent No.: US 6,290,831 B1
(45) Date of Patent: Sep. 18, 2001

(54) ELECTROPHORETIC SYSTEM FOR REAL TIME DETECTION OF MULTIPLE ELECTROPHORESED BIOPOLYMERS

(75) Inventors: Yoram Liran, Rehovot; Michael Tal, Bilu, both of (IL)

(73) Assignee: Integrated Genetic Devices, Ltd., Rehovot (IL)

( * ) Notice: Subject to any disclaimer, the term of this patent is extended or adjusted under 35 U.S.C. 154(b) by 0 days.

(21) Appl. No.: 09/384,996

(22) Filed: Aug. 30, 1999

(51) Int. Cl.$^7$ .......................................................... C02F 1/40
(52) U.S. Cl. ............................................. 204/612; 204/618
(58) Field of Search .................................. 204/456, 466, 204/467, 606, 616, 618, 451, 452, 601, 603

(56) References Cited

U.S. PATENT DOCUMENTS

| | | | |
|---|---|---|---|
| 4,683,195 | 7/1987 | Mullis et al. | 435/6 |
| 4,683,202 | 7/1987 | Mullis | 435/91.2 |
| 5,051,162 | * 9/1991 | Kambara et al. | 204/612 |
| 5,843,650 | 12/1998 | Segev | 435/6 |
| 5,846,709 | 12/1998 | Segev | 435/6 |
| 5,897,842 | 4/1999 | Dunn et al. | 422/131 |
| 6,015,902 | * 1/2000 | Bieniarz et al. | 546/105 |

FOREIGN PATENT DOCUMENTS

| | | | |
|---|---|---|---|
| 3092756 | * | 9/1987 | (JP) . |
| 362212561 A | * | 9/1987 | (JP) . |
| 402143145 A | * | 9/1987 | (JP) . |
| 401209351 A | * | 8/1989 | (JP) . |

OTHER PUBLICATIONS

JAPIO abstract of Yamada (JP 362212561 A), Sep. 1987.*
JAPIO abstract of Okubo (JP 401209351 A), Aug. 1989.*
Derwent abstract of Hitachi (JP 03092756 A), Sep. 1987.*
Japio abstract of Taira et al. (JP 402143145 A), Jun. 1990.*

* cited by examiner

Primary Examiner—Jill Warden
Assistant Examiner—Alex Noguerola (57) ABSTRACT

An electrophoretic system for real time analysis of a plurality of samples each containing at least one biopolymer is disclosed. The system includes (a) a holder for holding a plurality of removable gel cassettes, the holder supporting a plurality of electrode pairs electrically connectable to an external power source; (b) the plurality of removable gel cassettes each having an open top end and a bottom end and being designed for containing a gel slab therein, wherein each pair of the plurality of electrode pairs serves for creating a voltage gradient in a single gel slab, such that electrophoretic separation of the at least one biopolymer of each of the plurality of samples is effectable thereby; (c) a plurality of detector assemblies each including a plurality of detection units, each of the plurality of detector assemblies being intimately positionable at a region of one of the plurality of removable gel cassettes corresponding to a portion of the gel slab, each of the plurality of detector assemblies being for collecting information pertaining to at least one property of at least one biopolymer from the portion of the gel slab, whereas each of the plurality of detection units of a single detector assembly of the plurality of detector assemblies serves for collecting information pertaining to at least one property of at least one biopolymer in a subregion of the portion of the gel slab.

51 Claims, 5 Drawing Sheets

ELECTROPHORETIC SYSTEM FOR REAL TIME DETECTION OF MULTIPLE ELECTROPHORESED BIOPOLYMERS

FIELD AND BACKGROUND OF THE INVENTION

The present invention relates to an electrophoretic assembly and system, and a method of utilizing same, which are utilizable for the real-time analysis of biopolymers contained within a plurality of samples.

Electrophoresis, an analytical separation and analysis technique, has become an indispensable tool in science, particularly in the analysis of biological samples of biopolymers such as proteins, DNA and RNA.

Electrophoresis is based on the fact that, under the effect of an electric field, molecules migrate within a substrate medium at different speeds according to their charge density, size and conformation. Under electrophoretic conditions wherein charge density and conformation are constant, electrophoretic separation of biopolymers serves for determining the size of the electrophoresed biopolymers. Such conditions characterize linear double stranded nucleic acids in substantially natural environment, denatured single stranded nucleic acids (e.g., in presence of urea, formamide, formaldehyde, glyoxal) and denatured and reduced proteins (e.g., subjected to a reducing agent such as β-mercaptoethanol and denaturing and charge density forming agent sodium dodecyl sulfate).

Under electrophoretic conditions wherein charge density and size are constant, conformational changes between electrophoresed biopolymers are detectable. This is the case, for example, for circular nucleic acid molecules which can resume one of several conformational forms, depending on the level of super coiling, and for single or double stranded nucleic acid molecules which differ in sequence by as little as a single nucleotide per several hundred bases, as is the case is single stranded conformational polymorphism (SSCP) and in heteroduplex analyses.

In special cases electrophoresis is employed under (hanging conformational or charge conditions, such as in denaturing or temperature gradient gel electrophoresis (DGGE or TGGE) of nucleic acids and isoelectric focusing of proteins. In other cases, alternating electrical fields are employed for electrophoresis in what is known as pulse field gel electrophoresis.

Electrophoresis is generally carried out on a solid substrate such as a gel, for example, a polyaciylamide or agarose gel, within which the molecules to be analyzed migrate at different speeds according to the underlying principles described above.

After a given migration period, during which the molecules are subject to the effect of an electric field, they are displaced within the substrate by a given distance which is proportional to their speed of migration which correlates to their charge density, size and/or conformation. By employing a suitable detection, the regions reached by the different types of molecules at the end of a given time period can be displayed in the form of bands.

Many variations of the technique have been developed over the past two decades, including slab and tube (e.g., capillary tube) gel electrophoresis.

Dedicated equipment for carrying out the different types of electrophoresis has been developed and is commercially available. Such equipment includes systems for native and denaturative protein gel electrophoresis, protein isoelectric focusing gel electrophoresis, nucleic acids gel electrophoresis, nucleic acid sequencing gel electrophoresis, denaturing/temperature gradient gel electrophoresis and pulse field gel electrophoresis.

Present day commercially available electrophoretic apparatuses typically utilized for analytical electrophoresis suffer from a number of limitations.

Since most of the apparatuses employed for electrophoresis utilize a single gel slab, a limited number of samples can be co-analyzed.

As such, when processing a large number of samples, multiple electrophoretic runs are often necessary which can be time consuming and tedious to execute. In addition comparisons from samples or runs and particularly from different sample batches are very difficult since conditions of the electrophoresis vary and regulation and monitoring of the conditions is not available or unreliable. Thus, when resorting to multiple electrophoretic runs, a wide variation in determinations of molecular weight, as well as the properties of the sample components can be experienced. Overcoming this limitation requires the use of a large gel slab with a large sample number capacity which in turn requires the use of a relatively large and thus cumbersome apparatus. In addition, the large gel slab of such an apparatus would require a high electrical current, which causes over heating of the slab.

In order to overcome these limitations, and yet maintain a relatively small apparatus size, multiple gel slab apparatuses have been devised. For example, U.S. Pat. No. 5,047,135 discloses a gel electrophoresis system in which the gel slab is a multi-gel slab which is subdivided by means of thin divider sheets into wafer-like micro-gels. This composite slab gel is electrophoresed as a single slab gel, following which the micro-gels may be peeled off and separately processed.

Although this system enables multiple gel slabs to be electrophoresed in a relatively compact instrument, there is no possibility of performing real time and simultaneous analysis of the results.

Currently available gel electrophoretic apparatuses including multi-gel slab apparatuses suffer from another inherent limitation. These apparatuses usually do not prevent the sample from running off the gel, nor do they provide assurance that the sample has had sufficient time for a reasonable separation. Thus, to assure optimal separation without sample loss a user must closely monitor the apparatus when used. This limitation is especially inherent to multi gel slab apparatuses since in these apparatuses a variance in the separation can often be experienced from one gel slab to the next, which variance cannot always be detected by the user due to the configuration of the apparatus.

U.S. Pat. No. 5,275,710 describes an electrophoretic system for carrying out electrophoresis while monitoring and analyzing, in real time, samples electrophoretically separated thereby. Although this system overcomes some of the limitations described hereinabove it is still limited to use with a single gel slab and therefore it does not provide a user with means with which real time analysis of a large number of electrophoresed samples can be effected.

There is thus a widely recognized need for, and it would be highly advantageous to have, a gel electrophoresis system for processing a large number of samples which system enables a real-time analysis of biopolymers contained within each sample.

SUMMARY OF THE INVENTION

According to one aspect of the present invention there is provided an electrophoretic system for real time analysis of a plurality of samples each containing at least one biopolymer, the system comprising (a) a holder for holding a plurality of removable gel cassettes, the holder supporting a plurality of electrode pairs electrically connectable to an external power source; (b) the plurality of removable gel cassettes, each having an open top end and a bottom end and being designed for containing a gel slab therein, wherein each pair of the plurality of electrode pairs serves for creating a voltage gradient in a single gel slab, such that electrophoretic separation of the at least one biopolymer of each of the plurality of samples is effectable thereby; (c) a plurality of detector assemblies, each including a plurality of detection units, each of the plurality of detector assemblies being intimately positionable at a region of one of the plurality of removable gel cassettes corresponding to a portion of the gel slab, each of the plurality of detector assemblies being for collecting information pertaining to at least one property of at least one biopolymer from the portion of the gel slab, whereas each of the plurality of detection units of a single detector assembly of the plurality of detector assemblies serves for collecting information pertaining to at least one property of at least one biopolymer in a subregion of the portion of the gel slab.

According to another aspect of the present invention there is provided an electrophoretic device assembly comprising (a) a holder being for holding a plurality of removable gel cassettes each having open top and bottom ends and each being designed for containing a gel slab therein; (b) a plurality of electrode pairs, supported by the holder and being electrically connectable to an external power source; and (b) a plurality of detector assemblies attached to, or integrally formed with, the holder, each of the detector assemblies capable of intimately contacting a region of each of the plurality of removable gel cassettes when disposed in the holder.

According to yet another aspect of the present invention there is provided a method of real time analysis of a plurality of samples each containing at least one biopolymer, the method comprising the steps of (a) electrophoretically co-separating the plurality of samples in a plurality of gel cassettes each containing a gel slab with a plurality of sample wells; (b) concomitantly collecting information from a region of each of the plurality of removable gel cassettes, the information pertaining to at least one property of the at least one biopolymer; and (c) analyzing the information so as to determine the at least one property relating to the at least one biopolymer of each of the plurality of samples.

According to further features in preferred embodiments of the invention described below, the electrophoretic system further comprising (d) an analyzer being in communication with each of the plurality of detector assemblies, the analyzer being for analyzing the information collected from the region of at least one of the plurality of removable gel cassettes so as to determine at least one property of the at least one biopolymer.

According to still further features in the described preferred embodiments, the bottom end is an open end, the electrophoretic system further comprising (e) a gel top buffer chamber being, when filled with a buffer solution, in electrical communication with a plurality of first electrodes of the plurality of electrode pairs, the gel top buffer chamber including a wall provided with an aperture which establishes a sealing relationship with the open top end of the plurality of removable gel cassettes; and (f) a gel bottom buffer chamber being, when filled with the buffer solution, in electrical communication with a plurality of second electrodes of the plurality of electrode pairs, the gel bottom buffer chamber being for containing the open bottom end of the plurality of removable gel cassettes.

According to still further features in the described preferred embodiments the plurality of removable gel cassettes are disposed within the housing in a vertical wafer configuration.

According to still further features in the described preferred embodiments the gel slab is composed of a gel selected from the group consisting of a polyacrylamide gel, an agarose gel and a starch gel.

According to still further features in the described preferred embodiments each of said plurality of removable gel cassettes includes at least a portion made of a material which is substantially transparent to ultraviolet rays.

According to still further features in the described preferred embodiments the electrophoretic system further comprising a sample comb including a serrated edge or a set of teeth, adapted to be removably fitted into the open top end of each of the plurality of removable gel cassettes during casting of the gel slab to serve as a mold for a plurality of sample wells in the top of the gel slab.

According to still further features in the described preferred embodiments the at least one biopolymer is selected from the group consisting of a polynucleotide and a polypeptide.

According to still further features in the described preferred embodiments the electrophoretic system further comprising a cooling device adapted to cool the plurality of removable gel cassettes.

According to still further features in the described preferred embodiments each of the plurality of the detector assemblies is attached to, or integrally formed, with the housing.

According to still further features in the described preferred embodiments the region is located in a bottom portion of each of the removable gel cassettes.

According to still further features in the described preferred embodiments at least one of the plurality of detector assemblies is a radioactivity detector assembly adapted for collecting radioactive radiation emitted from the region of the one of the plurality of removable gel cassettes.

According to still further features in the described preferred embodiments at least one of the plurality of detector assemblies is an optical detector assembly adapted for collecting light radiation transmitted through, reflected, scattered or emitted from the region of the one of the plurality of removable gel cassettes.

According to still further features in the described preferred embodiments the optical detector assembly includes a light source serving for illuminating the region of one of the plurality of removable gel cassettes, and an optical detector serving for collecting light from the region of the at least one of the plurality of removable gel cassettes.

According to still further features in the described preferred embodiments the optical detector serves for collecting light transmitted through the region of the at least one of the plurality of removable gel cassettes.

According to still further features in the described preferred embodiments the optical detector serves for collecting light reflected, scattered or emitted from the at least one of the of plurality of removable gel cassettes.

According to still further features in the described preferred embodiments the light source and the optical detector each independently includes an optical fiber bundle.

According to still further features in the described preferred embodiments the optical detector further includes at least one deflector adapted for deflecting light collected from the region of the at least one of the plurality of removable gel cassettes onto the optical detector.

According to still further features in the described preferred embodiments the at least one deflector is selected from the group consisting of a prism, a lens assembly and a reflector.

According to still further features in the described preferred embodiments the at least one property of the at least one biopolymer is selected from the group consisting of molecular size and amount.

According to still further features in the described preferred embodiments the at least one biopolymer is fluorescently stained such that fluorescent light is collected by one of the plurality of detector assemblies from the region of the at least one of the plurality of removable gel cassettes when the at least one biopolymer migrates into the portion of the gel slab.

According to still further features in the described preferred embodiments the at least one biopolymer is a polynucleotide which is fluorescently stained with a polynucleotide intercalating fluorescent dye.

According to still further features in the described preferred embodiments the at least one biopolymer is radioactivity labeled such that radiation is collected by one of the plurality of detector assemblies from the region of the at least one of the plurality of removable gel cassettes when the at least one biopolymer migrates into the portion of the gel slab.

According to still further features in the described preferred embodiments the light source is selected from the group consisting of an incoherent light source and a coherent light source.

According to still further features in the described preferred embodiments the light source is an ultraviolet light source.

According to still further features in the described preferred embodiments said plurality of removable gel cassettes disposed in a vertical wafer configuration include m gel cassettes and further wherein each of said plurality of removable gel cassettes includes n sample wells so as to form a microtiter m×n sample well configuration, wherein n and m are each independently an integer greater than 1.

According to still further features in the described preferred embodiments at least a portion of the m×n sample wells are concomitantly loadable with the at least one biopolymer via a multisample handling device.

The present invention successfully addresses the shortcomings of the presently known configurations by providing an electrophoretic assembly and system, and a method of utilizing same, which are utilizable for the real-time analysis of biopolymers contained within a plurality of samples in a manner unprecedented so far.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIG. 1b is a front view of a gel cassette utilizable by the assembly of FIG. 1a;

DESCRIPTION OF THE PREFERRED EMBODIMENTS

The present invention is of an electrophoresis assembly and system, and a method of using same, which can be used for real time analysis of a plurality of samples, each containing at least one biopolymer. Specifically, the present invention can be used to retrieve information pertaining to at least one property of biopolymers contained within a plurality of samples.

The principles and operation of an assembly, system and method according to the present invention may be better understood with reference to the drawings and accompanying descriptions.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

Figure 1A:
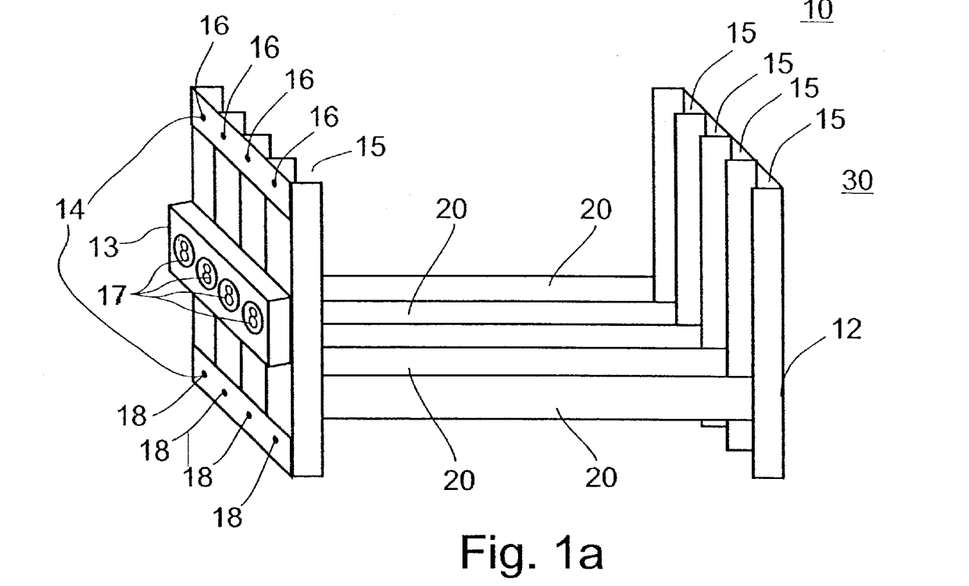
FIG. 1a is a perspective view of an electrophoretic assembly according to the present invention.

Referring now to the drawings, FIG. 1a illustrates the electrophoretic device assembly according to one aspect of the present invention, which is referred to hereinunder as assembly 10.

Figure 1B:
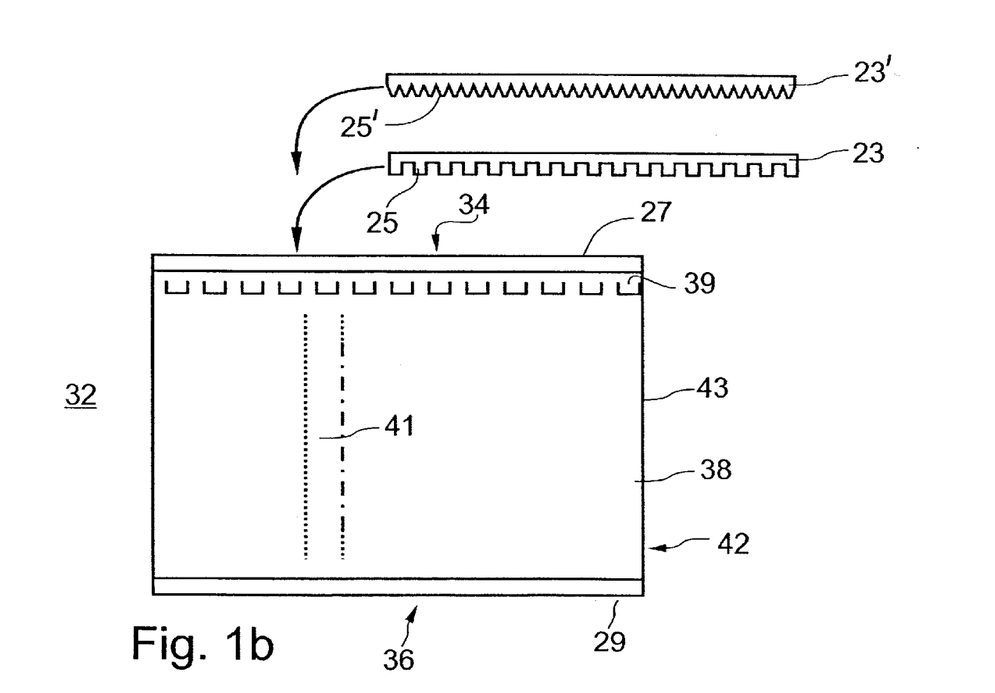

Assembly 10 includes a holder 12 which serves for holding a plurality of removable gel cassettes 32 (one is shown in FIG. 1b) within tight fitting grooves 15. Holder 12 is made of light metal or plastic and can be readily manufactured by methods well known in the art.

Gel cassettes 32 serve for electrophoretically separating samples of biopolymers. As seen in FIG. 1b removable gel cassette 32 has open top end 34 and open or closed bottom end 36 end, depending on the use of gel cassettes with or without buffer containers, respectively. Cassette 32 is designed for containing a gel slab 38 therein. As such, each cassette 32 is formed of a front plate 43 and a back plate 42. Plates 43 and 42 can be separated by spacers (not shown) or any other means so as to define a space there between. Cassette 32 further includes top and bottom electrically conductive strips 27 and 29 each running the width thereof.

Assembly 10 further includes a plurality of electrode pairs 14 (four pairs are shown) supported by holder 12. each of electrode pairs 14 includes a top electrode 16 and a bottom electrode 18. Electrodes 16 and 18 are each separately connectable to an external power source. Electrodes 16 and 18 serve to generate a voltage gradient within a gel slab of a gel cassette. To generate such voltage gradient, cassette 32 is configured of an appropriate size so as to fit within assembly 10 such that electrical contact is establishable between electrodes 16 and 18 and electrically conductive strips 27 and 29. The voltage gradient established within gel slab 38 enables electrophoretic separation of charged biopolymers contained within a sample or samples loaded thereon.

Assembly 10 is designed to hold any number of gel cassettes, preferably in a vertical wafer configuration. The number of gel cassettes may vary, but an arrangement of m gel plates each having n wells which conforms to an arrangement of a microtiter plate array or a portion thereof is preferred. For example, an m=8 by n=12 configuration is envisaged, wherein spacing between adjacent lanes in a gel cassette and in-between gel cassettes is designed so as to conform to the spacing between wells of a 96 well microtiter plate. Assembly 10 which is designed for holding 8 gel cassettes, will measure about 12×12×15 cm.

Using this configuration, samples prepared by a biological or chemical reaction, for example a PCR reaction, can be directly loaded onto cassettes held in assembly 10 of the present invention by, for example, the open capillaries of the device described in U.S. patent application Ser. No. 09/339, 865 or the open capillaries of the device described in U.S. Pat. No. 5,897,842, both of which are incorporated by reference as if fully set forth herein, as well as similar devices having an array of open capillaries which can be used to collect, hold and eject liquids.

This renders assembly 10 according to the present invention amenable to automatic sample loading. Since assembly 10 forms a part of an electrophoresis system according to the present invention, which system is further detailed hereinunder, the various stages of electrophoresis which include sample loading, electrophoresis and analysis can be performed without the intervention of a user.

Assembly 10 further includes a cooling device 13 which serves for removing excess heat produced mostly due to the light sources and the electrical resistance of gel slabs 38 of cassettes 32 to passage of electrical current therethrough. Cooling device 13 can be, for example, a fan 17 or preferably a plurality of fans, which direct air flow through the space formed between adjacent gel cassettes 32.

Assembly 10 further includes a plurality of detector assemblies 20 (four are shown) permanently or removably attached to holder 12. Each of detector assemblies 20 is positionable so as to intimately contact a region of cassette 32 when disposed within assembly 10. As is further described hereinbelow, detector assemblies 20 serve for collecting information from a region of a gel cassette disposed within holder 12, which information pertains to the biopolymers electrophorescd through gel slabs 38.

According to another aspect of the present invention and as shown in FIGS. 2–5, assembly 10 forms a part of an electrophoretic system which is referred to hereinunder as system 30.

Figure 2:
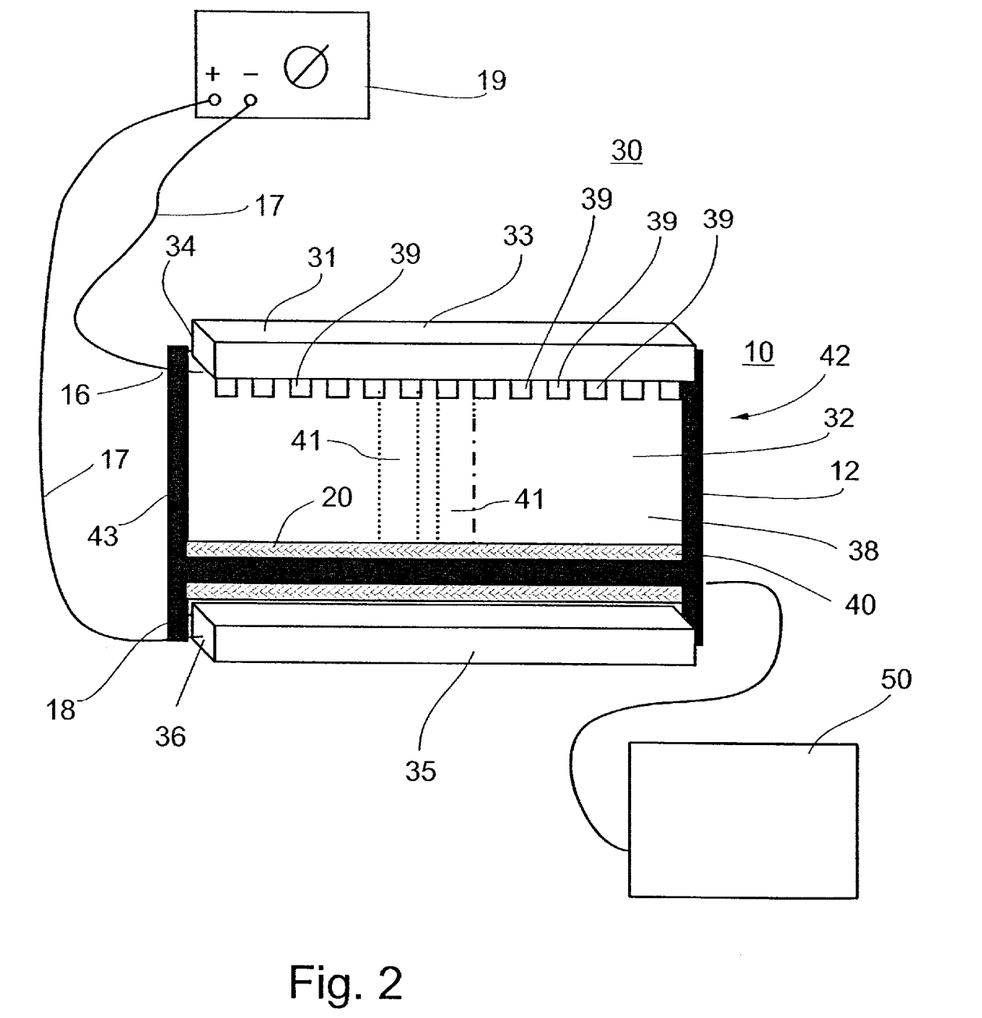
FIG. 2 is a front view of an electrophoretic system according to the present invention.

System 30 preferably serves to electrophoretically co-separate a plurality of samples in a plurality of cassettes 32. System 30 further provides means with which real time, concomitant analysis of the samples can be effected.

To effect separation of biopolymers by system 30, samples containing one or more biopolymers are loaded onto gel slab 38 from open top end 34 of cassette 32. Preferably, the samples are loaded into sample wells, the preparation or formation of which is further described hereinunder. Following loading, electrical current is applied to electrodes 16 and 18. Typically electrode 16 is a cathode and electrode 18 is an anode, since most electrophoretic separations are employed on negatively charged biopolymers. Upon generation of a voltage gradient along gel slab 38, the biopolymers contained within the sample migrate towards electrode 18 end of gel slab 38, each at a speed which correlates to one or more properties of the biopolymer and electrophoresis conditions, as further detailed in the Background section. As a result, electrophoretic separation of biopolymers contained within a sample is effected.

According to the present invention and as is further detailed hereinunder, information pertaining to the migration speed of each biopolymer contained within a sample is retrieved, which information is used according to preferred embodiments of the present invention to construct a virtual image depicting a pattern of the separated biopolymers, which pattern correlates to a property of the biopolymers. It will be appreciated that due to the configuration of system 30, a separation pattern can be obtained for each of the samples co-separated on a plurality of gel slabs 38 simultaneously. In addition, since system 30 of the present invention employs real-time detection of biopolymers, this pattern is obtained without the need for visualization processing (e.g., imaging, photographing) gel slabs 38 following electrophoresis.

Preferably, system 30 is a bufferless electrophoresis system in which electrodes 16 and 18 are directly connected to gel slab 38 through strips 27 and 29. Bufferless electrophoresis depends on a buffer contained within the gel matrix to provide for electrical conductiveness. Bufferless electrophoresis is advantageous since it negates the need for cumbersome buffer chambers and complicated sealing schemes.

It will be appreciated that although the use of buffer chambers is disadvantageous, in some respects, the use thereof does provide some benefit especially in establishing and maintaining a constant voltage gradient within a multiplicity of gel slabs 38.

Thus, according to one embodiment of the present invention, system 30 further includes a gel top buffer chamber 31. Gel top buffer chamber 31 includes a bottom wall 33 provided with multiple apertures, each establishing a sealing relationship with open top end 34 of each of gel cassettes 32. System 30 further includes a gel bottom buffer chamber 35 which serves for containing open bottom end 36 of removable gel cassettes 32. In this configuration system 30 can utilize only a single electrode 16 within buffer chamber 31 and a single electrode 18 within buffer chamber 35. It will be appreciated that in this case, cassettes 32 do not contain the electrically conducting strips mentioned hereinabove with respect to the presently preferred bufferless configuration.

As mentioned hereinabove, cassette 32 includes a gel slab 38 therein. Gel slab 38 is a semi-solid matrix which can be composed of, for example, polyacrylamide, agarose or starch, complexed with water or a buffer to form a semi-solid substance of defined porosity. The porosity of gel slab 38 is determined by the concentration and physical properties of the gel material. Gel slab 38 is formed within the space defined between plates 43 and 42 by methods well known in the art. For example, agarose dissolved in an aqueous solution can be poured into this space following which the dissolved agarose cools and congeals (gelates) to form a semi-solid gel matrix. It will be appreciated in this respect that since gel slab 38 is preferably utilized for the electrophoretic separation of a plurality of samples, prior to congealing, a sample comb 23 (FIG. 1*b*) having teeth 25, can be inserted into open top end 34 of cassette 32 to serve as a mold for a plurality of sample wells 39 formed in the top of gel slab 38. Alternatively, a serrated comb 23' (FIG. 1*b*) is contacted with the top portion of the gel to form wells among teeth 25' thereof. It will be appreciated that cassettes 32 according to the present invention can be provided as disposable precast cassettes or alternatively cassettes 32 can be provided as reusable cassettes in which multiple recasting of gel slab 38 can be effected by a user.

As already mentioned hereinabove assembly 10 which forms a part of system 30 according to this aspect of the present invention includes a plurality of detector assemblies 20. As specifically seen in FIG. 2 each detector assembly 20 is intimately positionable at a region 40 on front plate 43 and/or back plate 42 of each gel cassette 32, which region 40 corresponds to a portion of gel slab 38. Detector assembly 20 serves for collecting information pertaining to at least one property of a biopolymer contained within a sample electrophoretically separated in gel slab 38. It will be appreciated that when gel slab 38 is utilized for electrophoretic separation of multiple samples, each loaded into a sample well 39, a vertical lane 41 is defined for each sample during electrophoresis. In such a case, when samples are electrophoresed, detector assembly 20 simultaneously collects information from each sample at region 40 of each vertical lane 41. Detector assembly 20 is configured such that it can retrieve information from detection units defining subregions of region 40. As further detailed hereinunder, detection units can be of any size which dictates the resolution of the detector assembly 20.

System 10 further includes an analyzer 50. Analyzer 50 is in communication with each detector assembly 20 and serves for analyzing information collected thereby.

According to the present invention detection of biopolymers contained within a sample can be provided by one of several detector types.

Thus according to one preferred embodiment of the present invention detector assembly 20 is an optical detector assembly.

Figure 3:
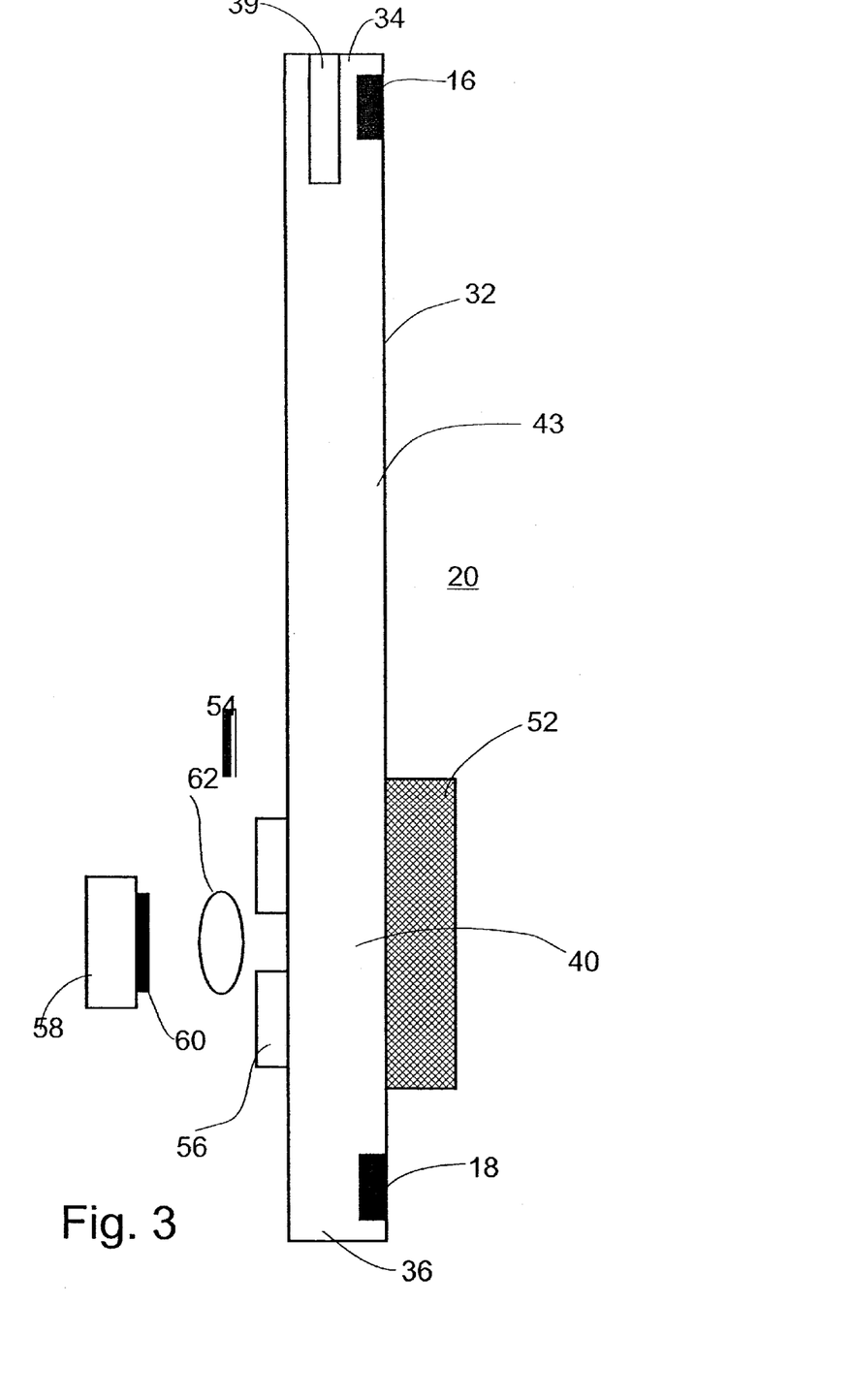
FIG. 3 is a side view of a single gel cassette of the system shown in FIG. 2, depicting one embodiment of a detector assembly of the present invention.

As specifically seen in FIG. 3 which is a side view of a single gel cassette 32, detector assembly 20 includes a light source 52 disposed in intimate contact with region 40 of front plate 43. Light source 52 can include a light waveguide, such as, but not limited to, an optical fiber bundle, which is optically coupled to a light generator, disposed, for example, within analyzer 50. Alternatively, light source 52 can include an array of light emitting diodes, lamps or similar devices which are in electrical communication with a power and modulation device disposed in analyzer 50. Light source 52 serves for illuminating a portion of gel slab 38 which corresponds to region 40.

Detector assembly 20 further includes an optical mask 54 positioned in intimate contact with back plate 42 at region 40. Optical mask 54 serves for creating a slit 56 within region 40 such that light from light source 52 transmitted through, scattered or emitted from, region 40 of gel cassette 32 is partially masked by optical mask 54 and its passage restricted by the dimensions of slit 56. Slit 56 can either be continuous along the width of cassette 32 or alternatively it can be discontinuous, in which case slit 56 is divided into apertures each substantially covering a single vertical lane width. Slit 56 is typically selected of maximal height which corresponds to the height of a typical biopolymer band. Thus, slit 56 is selected of a height within a range of 0.05 mm to 5 mm, more preferably 0.3 mm to 1 mm.

Detector assembly 20 further includes an optical detector 58 which is aligned with, and is in close proximity to, slit 56. Optical detector 58 is electrically coupled to analyzer 50. The vertical dimension of optical detector 58 is preferably selected small enough so as to image slit 56 with high vertical resolution. In one possible configuration optical detector 58 is placed very close (preferably much less than 1 mm) to slit 56 in a so-called "proximity configuration", in which case there is no need for imaging optics between slit 56 and detector 58. This configuration has the advantage of being very thin. In another possible configuration, the configuration which is shown in FIG. 2, the detector is placed at some distance from the slit and a lens 62 is used to collect and focus light from the slit 56 onto the detector 58. Optical detector 58 can be, for example, a linear or two dimensional CCD array of any number of CCD elements (for example, Kodak KLI series, Eastman Kodak Company, Rochester N.Y.; Dalsa IL-CC series or IT-F6 series, Dalsa Inc. Waterloo Ontario, Canada) or a linear or a two dimensional array of Si photodiodes (for example, UDT series A5C or A5V, UDT Sensors Inc. Hawthorne Calif.; Hamamatsu series S4113, Hamamatsu Bridgewater N.J.). In this case optical detector 58 is electrically coupled to analyzer 50 such that collected light is converted into an electrical signal which is thereafter relayed to analyzer 50 for analysis. When low intensity light is to be detected, system 10 is preferably covered by a light tight cover, so as to prevent interference with detection by surrounding light. For some applications, detector 58 is selected so as to provide distinguishable detection to several, e.g., fluorescent, wavelengths. This can be achieved, for example, by the use a filters wheel, rotatable in front of detector 58.

Alternatively, detector assembly 20 can include a light vvaveguide, such as, but not limited to, an optical fiber bundle having closely spaced fibers (e.g., 0.05–0.1 mm) in order to maintain high spatial resolution. In this case, collected light is optically relayed to analyzer 50 for analysis.

Figure 4:
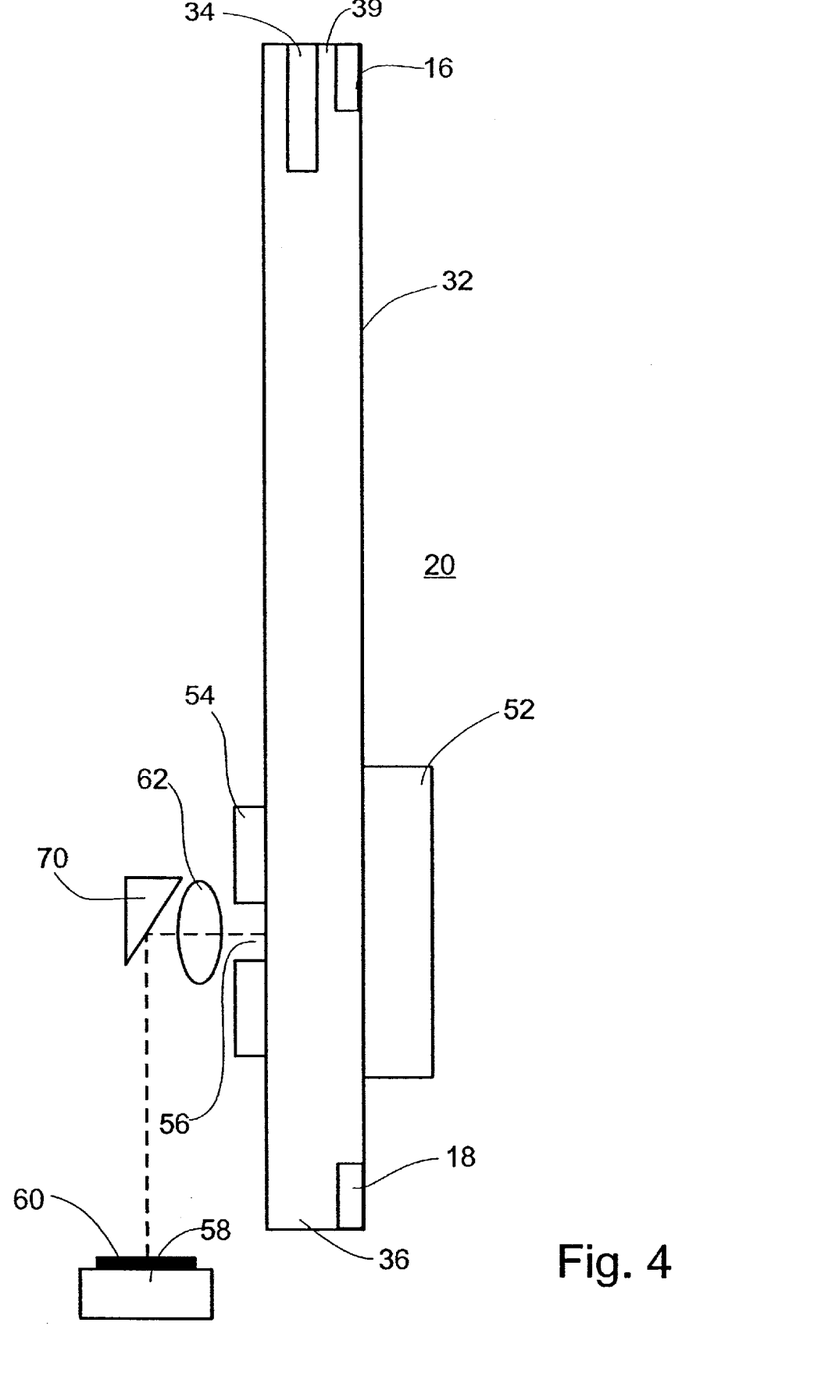
FIG. 4 is a side view of a single gel cassette of the system shown in FIG. 2, depicting another embodiment of a detector assembly of the present invention.

In an alternative configuration of detector assembly 20, and as specifically shown in FIG. 4, optical detector 58 is disposed below bottom end 36 of cassette 32. In such a configuration, light passing through slit 56 is redirected by a deflector 70 onto detector 58. This configuration is advantageous since a single optical detector 58 can be employed to collect light from a plurality of gel cassettes 32. In addition, placing optical detector 58 below gel cassette 32 enables to minimize the gap between adjacent cassettes 32 and as such to substantially reduce the bulk of system 30. It will be appreciated that this configuration is best utilized in a bufferless system 30 which does not include buffer chambers 31 and 35, or in a system that has a thin buffer chamber at the bottom of the slab. Deflector 70 can be, for example, a reflector such as a mirror, a lens assembly, a prism or a bundle of optical fibers incorporable directly into slit 56 so as to reduce bulk. Alternatively, optical detector 58 can be positioned along the side of assembly 10, in which case deflector 70 is used to deflect light in a direction enabling the use of this configuration with buffer chambers.

Optionally and presently preferably, detector assembly 20 further includes an optical filter 60 and a lens 62 disposed between slit 56 and optical detector 58. Filter 60 can be, for example, a spectral filter or a polarizing filter and serves to filter the light passing through slit 56 from any unwanted or interfering light which does not originate in light source 52, while at the same time, efficiently transmitting a specific wavelength or wavelengths, thus increasing the signal-to-noise ratio and sensitivity of light collection by optical detector 58. In cases of fluorescence, as further detailed hereinunder, filter 60 serves to substantially filter-out wavelengths originating from source 52, so as to enable specific detection of the fluorescence caused. Lens 62 serves to collimate or focus light transmitted though slit 56. In this configuration optical detector 58 can be co-fabricated with filter 60.

Detector assembly 20 is connected to a processing unit provided within analyzer 50 such that an electrical or optical output originating from Detector assembly 20 is processed by the processing unit.

Optical detection according to these embodiments of detector assembly 20 can be effected for a variety of biopolymers including polynucleotides and polypeptides. For example, a polynucleotide molecule can be optically detected when stained with a polynucleotide intercalating fluorescent dye, such as, for example ethidium bromide, propidium iodide and/or acridine orange. In this case, when a fluorescently labeled polynucleotide migrates within region 40, ultraviolet light from image source 52 produces fluorescence which is collected by optical detector 58 and relayed to analyzer 50. Upon processing in analyzer 50, the polynucleotide is represented as a fluorescent band which is defined by any number of picture elements (pixels) according to the resolution of optical detector 58 and to the size of slit 56. It will be appreciated that in the case where ultraviolet light is used for detection, at least one of plates 43 and 42 of gel cassette 32 are composed of a material which is substantially transparent to ultraviolet light such as but not limited to certain plastics.

Optical detection can also be applied to any biopolymer labeled with any fluorescent molecule. For example, a polypeptide labeled with a fluorophore such as, but not limited to, FITC, rhodamine, SPECTRUMORANGE, SPECTRUMGREEN, Aqua and/or Texas-Red, can also be detected. It will be appreciated that since different fluorophores have different excitation wavelengths, light source 52 is selected having a broad bandpass so as to match a plurality of fluorophores employable. It will also be appreciated that detector assembly 20 can be specifically configured so as to enable optimal detection of specific fluorescent molecules, by providing it with a suitable filter 60. It will further be appreciated that if detection in this case is utilized for determining the molecular size of a labeled biopolymer, as is further detailed hereinbelow, consideration must be given to the contribution of the label to the overall molecular size of the molecule.

Detector assembly 20 can also be utilized to detect fluorescence from polypeptides which include aromatic residues, such as tryptophan, tyrosine and phenylalanine by providing light of a specific wavelength suitable for the excitation and detection of these residues, as well known in the art.

Figure 5:
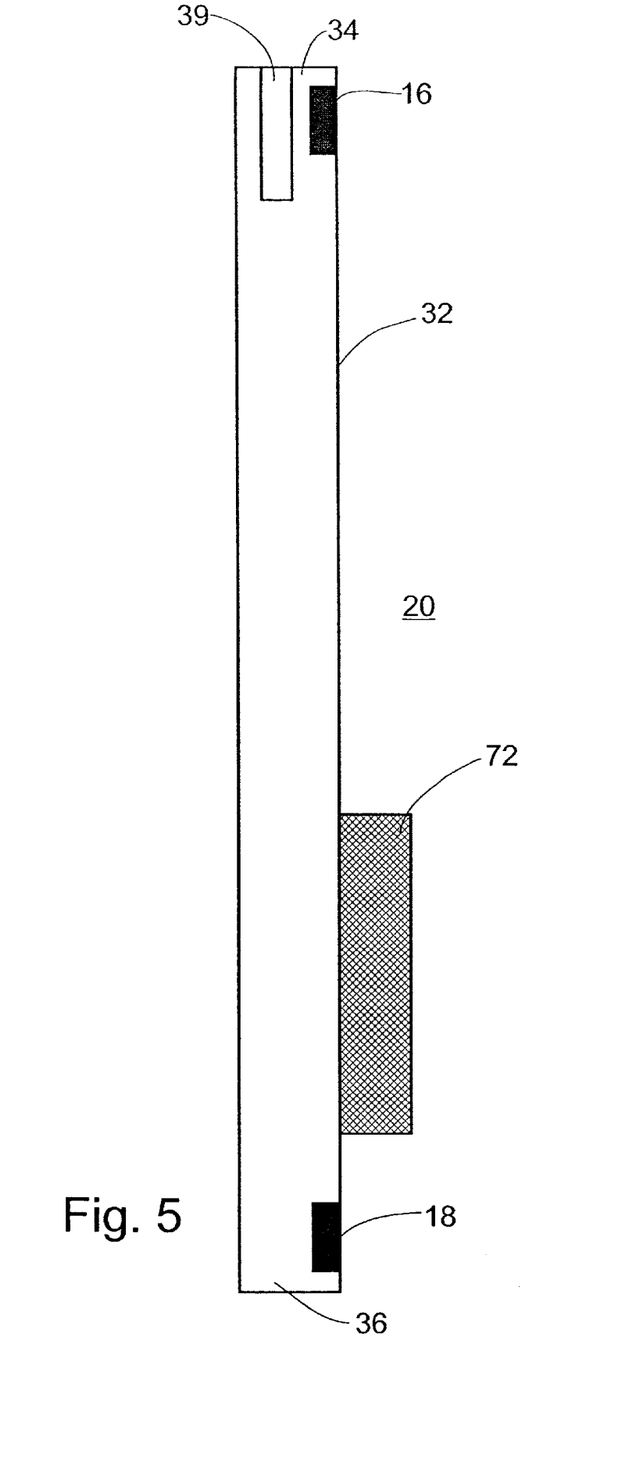
FIG. 5 is a side view of a single gel cassette of the system shown in FIG. 2, depicting yet another embodiment of a detector assembly of the present invention.

According to another preferred embodiment of the present invention and as specifically shown in FIG. 5 detector assembly 20 is a radioactivity detector 72. Detector 72 serves for detecting radioactive radiation in region 40 of gel cassette 32. It will be appreciated that such a detector is useful only in cases where radioactively labeled biopolymers are electrophoresed through gel slab 38. Radiation detector 72 is electrically coupled to analyzer 50, such that radioactive radiation information can be relayed to analyzer 50. According to this embodiment of the present invention region 40 is selected narrow enough so as to allow detection of radioactive radiation from a narrow portion of gel slab 38 which corresponds a maximal height of a biopolymer band.

As mentioned hereinabove, detector assembly 20 serves for collecting information pertaining to at least one property of a biopolymer or biopolymers contained within an electrophoresed sample.

According to a preferred embodiment of the present invention the at least one property of the biopolymer is its molecular size.

Since biopolymers contained within a sample migrate at different speeds when electrophoresed, which speed depends on at least one factor which is further discussed hereinabove, detection of each biopolymer of a sample, by detector assembly 20, occurs at a different time period from onset of electrophoresis.

For example, when electrophoresing polypeptides under denaturing conditions in which an equal charge density exists for the biopolymers of a sample, the vertical passage of a biopolymer in front of detector assembly 20 as a function of time, is inversely proportional to the size thereof.

Thus, as a band corresponding to a biopolymer is scanned across region 40, for example through slit 56, as is in the case for an optical detector assembly, the intensity of the band is integrated over time. At the same time, data pertaining to the band is recorded by the processing is unit of analyzer 50.

Thus, an electropherogram, which is a plot of signal intensity versus time, is formed for each lane in gel cassettes 38. These electropherograms, are analyzed by analyzer 50 which displays the results in real-time by, for example, a display screen. At the end of electrophoreses, accumulated gel electropherograms are stored in analyzer 50. A software program is preferably used to translate the electropherogram information into a molecular size for each band, using a reference electropherogram of known molecular standards co-separated within the same gel slab 38, or by standardizing a time versus molecular size relationship for each gel type and gel porosity. Standardizing can be especially effective in cases were a precast gel slab 38 is used since uniformity in the porosity between different batches is higher than that of user casted gel slabs 38. It will be appreciated that standardizing also requires the use of molecular standards, but only in order to establish a time versus molecular size relationship which can then be used to determine molecular size of future electrophoretic separations.

According to one embodiment of the present invention, information from the electropherograms can be presented to a user as graph or numerical data.

It will however be appreciated that users of prior art electrophoretic methods are accustomed to viewing separated biopolymers as a banded pattern image.

As such, according to another embodiment of the present invention analyzer 50 reproduces from the electrophergrams the shape and exact position of the bands in each lane, thus producing an image of bands typically produced by prior art electrophoretic methods. It will be appreciated that the shape of the band reproduced depends to a large extent on the resolution of the detector type. For example, in the case of optical detector 58 which includes photodiodes, the dimensions of the elements within optical detector 58 and their pitch are too large for high-resolution imaging. In this case, slit 56 is provided such that it covers only the height of a single band or less, such that the information obtained includes only the integral intensity and the position of the band which defines the molecular size, but not the particular shape of the band. Nevertheless, detector assembly 20 produces spatial information sufficient for the identification of bands and discrimination against various artifacts.

In cases where a CCD array or other high resolution detectors are used, the specific band shape can be reproduced. This is particularly advantageous in cases where a biopolymer band is irregularly shaped. In addition, as further detailed hereinbelow a detector with high resolution can more accurately predict the amount of a biopolymer present in a sample.

Thus, the information gathered from each biopolymer band can also be used to obtain data pertaining to the amount of biopolymer present in a sample. It will be appreciated that the intensity of signal collected from a biopolymer band, which is represented as the area of an electropherogram peak for that band directly correlates to the number of biopolymer molecules present within the band and/or to their molecular size. As such, the signal intensity information collected for a specific band can be compared to standards of known amounts and molecular sizes to yield the amount of the biopolymer present in the band. For example, a signal obtained from an ethidium bromide stained polynucleotide band of a calculated size can be compared to the signal obtained from polynucleotide standards of known sizes and amounts which are similarly stained and co-electrophoresed within the same gel slab 38, on one of the gel lanes.

In addition, the present invention can be used for polychromatic detection effected on a sample of biopolymers containing a plurality of fluorophore types. By utilizing an appropriate filter 60 and optical detector 58 each independent fluorophore is individually identifiable by the optical detector embodiment of detector assembly 20 of the present invention. The ability to discern between various fluorophore types greatly enhances the accuracy of system 30 in predicting molecular size of biopolymers because in this case a standard and an unknown biopolymer sample can be co-separated in the same lane. This can be effected providing the standard is labeled with a fluorophore which is excitable by the same wavelength of light as the biopolymers but yet which emits a different wavelength than that of the biopolyiner. This procedure enables accurate comparison of results between various lanes in the same gel and between results from different gels.

Thus, the present invention provides an electrophoretic assembly which is configured such that the sample wells of gel cassettes disposed therein form an array which spatially conforms to an array of microtiter plates and as such concomitant loading of a plurality of sample from automated sample handling devices adapted for use with micro titer plates can be effected. In addition the present invention also provides an electrophoretic system employing the assembly of the present invention, which system can be used for automated, real time analysis of individual biopolymers of a plurality of biopolymer samples. Furthermore, since the system of the present invention enables the electrophoresis i plurality of gel cassettes, several different types of gels each containing, for example, the same samples, can be simultaneously co-electrophoresed and the information collected from each used to analyze these samples.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

What is claimed is:

1. An electrophoretic system for real time analysis of a plurality of samples each containing at least one biopolymer, the system comprising:
   (a) a holder for holding a plurality of removable gel cassettes, said holder supporting a plurality of electrode pairs electrically connectable to an external power source;
   (b) said plurality of removable gel cassettes each having an open top end and a bottom end and being designed for containing a gel slab therein, wherein each pair of said plurality of electrode pairs serves for creating a voltage gradient in a single gel slab, for effecting electrophoretic separation of the at least one biopolymer of each of the plurality of samples; and
   (c) a plurality of detector assemblies, each including a plurality of detection units, each of said plurality of detector assemblies being intimately positionable at a region of one of said plurality of removable gel cassettes corresponding to a portion of said gel slab, each of said plurality of detector assemblies being for collecting information pertaining to at least one property of at least one biopolymer from said portion of said gel slab, whereas each of said plurality of detection units of a single detector assembly of said plurality of detector assemblies serves for collecting information pertaining to at least one property of at least one biopolymer in a subregion of said portion of said gel slab;
   wherein at least one of said plurality of detector assemblies is an optical detector assembly adapted for collecting light radiation transmitted through, reflected, scattered or emitted from said region of said one of said plurality of removable gel cassettes;
   said optical detector assembly includes a light source for illuminating said region of one of said plurality of removable gel cassettes, and an optical detector for collecting light from said region of said region of said at least one of said plurality of removable gel cassettes; and
   said optical detector further includes at least one deflector adapted for deflecting light collected from said region of said at least one of said plurality of removable gel cassettes onto said optical detector.

2. The electrophoretic system of claim 1, further comprising:
   (d) an analyzer being in communication with each of said plurality of detector assemblies, said analyzer being for analyzing said information collected from said region of at least one of said plurality of removable gel cassettes so as to determine at least one property of said at least one biopolymer.

3. The electrophoretic system of claim 1, wherein said bottom end is an open end, the system further comprising:
   (e) a gel top buffer chamber being, when filled with a buffer solution, in electrical communication with a plurality of first electrodes of said plurality of electrode pairs, said gel top buffer chamber including a wall provided with an aperture which establishes a sealing relationship with said open top end of said plurality of removable gel cassettes; and
   (f) a gel bottom buffer chamber being, when filled with said buffer solution, in electrical communication with a plurality of second electrodes of said plurality of electrode pairs, said gel bottom buffer chamber being for containing said open bottom end of said plurality of removable gel cassettes.

4. The electrophoretic system of claim 1, wherein said plurality of removable gel cassettes are disposed within said housing in a vertical wafer configuration.

5. The electrophoretic system of claim 4, wherein said plurality of removable gel cassettes disposed in a vertical wafer configuration include m gel cassettes and further wherein each of said plurality of removable gel cassettes includes n sample wells so as to form a microtiter m×n sample well configuration, wherein n and m are each independently an integer greater than 1.

6. The electrophoretic system of claim 5, wherein at least a portion of said m×n sample wells are concomitantly loadable with the at least one biopolymer via a multisample handling device.

7. The electrophoretic system of claim 1, wherein said gel slab is composed of a gel selected from the group consisting of a polyacrylamide gel, an agarose gel and a starch gel.

8. The electrophoretic system of claim 1, wherein each of said plurality of removable gel cassettes includes at least a portion made of a material which is substantially transparent to ultraviolet rays.

9. The electrophoretic system of claim 1, further comprising a sample comb including a serrated edge or a set of teeth, adapted to be removably fitted into said open top end of each of said plurality of removable gel cassettes during casting of said gel slab to serve as a mold for a plurality of sample wells in the top of said gel slab.

10. The electrophoretic system of claim 1, wherein said at least one biopolymer is selected from the group consisting of a polynucleotide and a polypeptide.

11. The electrophoretic system of claim 1, further comprising a cooling device adapted to cool said plurality of removable gel cassettes.

12. The electrophoretic system of claim 1, wherein each of said plurality of said detector assemblies is attached to, or integrally formed, with said housing.

13. The electrophoretic system of claim 1, wherein said region is located in a bottom portion of each of said removable gel cassettes.

14. The electrophoretic system of claim 1, wherein said optical detector serves for collecting light transmitted through said region of said at least one of said plurality of removable gel cassettes.

15. The electrophoretic system of claim 1, wherein said optical detector serves for collecting light reflected, scattered or emitted from said at least one of said of plurality of removable gel cassettes.

16. The electrophoretic system of claim 1, wherein said light source and said optical detector each independently includes an optical fiber bundle.

17. The electrophoretic system of claim 1, wherein said at least one deflector is selected from the group consisting of a prism, a lens assembly and a reflector.

18. The electrophoretic system of claim 1, wherein said at least one property of said at least one biopolymer is selected from the group consisting of molecular size and amount.

19. The electrophoretic system of claim 1, wherein said at least one biopolymer is fluorescently stained such that fluorescent light is collected by one of said plurality of detector assemblies from said region of said at least one of said plurality of removable gel cassettes when said at least one biopolymer migrates into said portion of said gel slab.

20. The electrophoretic system of claim 19, wherein said at least one biopolymer is a polynucleotide which is fluorescently stained with a polynucleotide intercalating fluorescent dye.

21. The electrophoretic system of claim 1, wherein said light source is selected from the group consisting of an incoherent light source and a coherent light source.

22. The electrophoretic system of claim 1, wherein said light source is an ultraviolet light source.

23. An electrophoretic system for real time analysis of a plurality of samples each containing at least one biopolyrrer, the system comprising:
   (a) a holder for holding a plurality of removable gel cassettes, said holder supporting a plurality of electrode pairs electrically connectable to an external power source;
   (b) said plurality of removable gel cassettes each having an open top end and a bottom end and being designed for containing a gel slab therein, wherein each pair of said plurality of electrode pairs serves for creating a voltage gradient in a single gel slab, for effecting electrophoretic separation of the at least one biopolymer of each of the plurality of samples; and
   (c) a plurality of detector assemblies, each including a plurality of detection units, each of said plurality of detector assemblies being intimately positionable at a region of one of said plurality of removable gel cassettes corresponding to a portion of said gel slab, each of said plurality of detector assemblies being for collecting information pertaining to at least one property of at least one biopolymer from said portion of said gel slab, whereas each of said plurality of detection units of a single detector assembly of said plurality of detector assemblies serves for collecting information pertaining to at least one property of at least one biopolymer in a subregion of said portion of said gel slab, wherein at least one of said plurality of detector assemblies is a radioactivity detector assembly adapted for collecting radioactive radiation emitted from said region of said one of said plurality of removable gel cassettes.

24. The electrophoretic system of claim 23, further comprising:
   (d) an analyzer being in communication with each of said plurality of detector assemblies, said analyzer being for analyzing said information collected from said region of at least one of said plurality of removable gel cassettes so as to determine at least one property of said at least one biopolymer.

25. The electrophoretic system of claim 23, wherein said bottom end is an open end, the system further comprising:
   (e) a gel top buffer chamber being, when filled with a buffer solution, in electrical communication with a plurality of first electrodes of said plurality of electrode pairs, said gel top buffer chamber including a wall provided with an aperture which establishes a sealing relationship with said open top end of said plurality of removable gel cassettes; and
   (f) a gel bottom buffer chamber being, when filled with said buffer solution, in electrical communication with a plurality of second electrodes of said plurality of electrode pairs, said gel bottom buffer chamber being for containing said open bottom end of said plurality of removable gel cassettes.

26. The electrophoretic system of claim 23, wherein said plurality of removable gel cassettes are disposed within said housing in a vertical wafer configuration.

27. The electrophoretic system of claim 26, wherein said plurality of removable gel cassettes disposed in a vertical wafer configuration include m gel cassettes and further wherein each of said plurality of removable gel cassettes includes n sample wells so as to form a microtiter m×n sample well configuration, wherein n and m are each independently an integer greater than 1.

28. The electrophoretic system of claim 27, wherein at least a portion of said m×n sample wells are concomitantly loadable with the at least one biopolymer via a multisample handling device.

29. The electrophoretic system of claim 23, wherein said gel slab is composed of a gel selected from the group consisting of a polyacrylamide gel, an agarose gel and a starch gel.

30. The electrophoretic system of claim 23, wherein each of said plurality of removable gel cassettes includes at least a portion made of a material which is substantially transparent to ultraviolet rays.

31. The electrophoretic system of claim 23, further comprising a sample comb including a serrated edge or a set of teeth, adapted to be removably fitted into said open top end of each of said plurality of removable gel cassettes during casting of said gel slab to serve as a mold for a plurality of sample wells in the top of said gel slab.

32. The electrophoretic system of claim 23, wherein said at least one biopolymer is selected from the group consisting of a polynucleotide and a polypeptide.

33. The electrophoretic system of claim 23, further comprising a cooling device adapted to cool said plurality of removable gel cassettes.

34. The electrophoretic system of claim 23, wherein each of said plurality of said detector assemblies is attached to, or integrally formed, with said housing.

35. The electrophoretic system of claim 23, wherein said region is located in a bottom portion of each of said removable gel cassettes.

36. The electrophoretic system of claim 23, wherein said at least one property of said at least one biopolymer is selected from the group consisting of molecular size and amount.

37. The electrophoretic system of claim 23, wherein said at least one biopolymer is radioactively labeled such that radiation is collected by one of said plurality of detector assemblies from said region of said at least one of said plurality of removable gel cassettes when said at least one biopolymer migrates into said portion of said gel slab.

38. An electrophoretic system for real time analysis of a plurality of samples each containing at least one biopolymer, the system comprising:

(a) a holder for holding a plurality of removable gel cassettes, said holder supporting a plurality of electrode pairs electrically connectable to an external power source;

(b) said plurality of removable gel cassettes each having an open top end and a bottom end and being designed for containing a gel slab therein, wherein each pair of said plurality of electrode pairs serves for creating a voltage gradient in a single gel slab, for effecting electrophoretic separation of the at least one biopolymer of each of the plurality of samples; and (c) a plurality of detector assemblies, each including a plurality of detection units, each of said plurality of detector assemblies being intimately positionable at a region of one of said plurality of removable gel cassettes corresponding to a portion of said gel slab, each of said plurality of detector assemblies being for collecting information pertaining to at least one property of at least one biopolymer from said portion of said gel slab, whereas each of said plurality of detection units of a single detector assembly of said plurality of detector assemblies serves for collecting information pertaining to at least one property of at least one biopolymer in a subregion of said portion of said gel slab;

wherein said at least one biopolymer is radioactively labeled such that radiation is collected by one of said plurality of detector assemblies from said region of said at least one of said plurality of removable gel cassettes when said at least one biopolymer migrates into said portion of said gel slab.

39. The electrophoretic system of claim 38, further comprising:

(d) an analyzer being in communication with each of said plurality of detector assemblies, said analyzer being for analyzing said information collected from said region of at least one of said plurality of removable gel cassettes so as to determine at least one property of said at least one biopolymer.

40. The electrophoretic system of claim 38, wherein said bottom end is an open end, the system further comprising:

(e) a gel top buffer chamber being, when filled with a buffer solution, in electrical communication with a plurality of first electrodes of said plurality of electrode pairs, said gel top buffer chamber including a wall provided with an aperture which establishes a sealing relationship with said open top end of said plurality of removable gel cassettes; and (f) a gel bottom buffer chamber being, when filled with said buffer solution, in electrical communication with a plurality of second electrodes of said plurality of electrode pairs, said gel bottom buffer chamber being for containing said open bottom end of said plurality of removable gel cassettes.

41. The electrophoretic system of claim 38, wherein said plurality of removable gel cassettes are disposed within said housing in a vertical wafer configuration.

42. The electrophoretic system of claim 41, wherein said plurality of removable gel cassettes disposed in a vertical wafer configuration include m gel cassettes and further wherein each of said plurality of removable gel cassettes includes n sample wells so as to form a microtiter m×n sample well configuration, wherein n and m are each independently an integer greater than 1.

43. The electrophoretic system of claim 42, wherein at least a portion of said m×n sample wells are concomitantly loadable with the at least one biopolymer via a multisample handling device.

44. The electrophoretic system of claim 38, wherein said gel slab is composed of a gel selected from the group consisting of a polyacrylamide gel, an agarose gel and a starch gel.

45. The electrophoretic system of claim 38, wherein each of said plurality of removable gel cassettes includes at least a portion made of a material which is substantially transparent to ultraviolet rays.

46. The electrophoretic system of claim 38, further comprising a sample comb including a serrated edge or a set of teeth, adapted to be removably fitted into said open top end of each of said plurality of removable gel cassettes during casting of said gel slab to serve as a mold for a plurality of sample wells in the top of said gel slab.

47. The electrophoretic system of claim 38, wherein said at least one biopolymer is selected from the group consisting of a polynucleotide and a polypeptide.

48. The electrophoretic system of claim 38, further comprising a cooling device adapted to cool said plurality of removable gel cassettes.

49. The electrophoretic system of claim 38, wherein each of said plurality of said detector assemblies is attached to, or integrally formed, with said housing.

50. The electrophoretic system of claim 38, wherein said region is located in a bottom portion of each of said removable gel cassettes.

51. The electrophoretic system of claim 38, wherein said at least one property of said at least one biopolymer is selected from the group consisting of molecular size and amount.

* * * * *